United States Patent
Yoo et al.

(10) Patent No.: US 11,172,944 B2
(45) Date of Patent: Nov. 16, 2021

(54) SMART SURGICAL INSTRUMENTS FOR ARTIFICIAL JOINT REPLACEMENT

(71) Applicant: CORENTEC CO., LTD., Chungcheongnam-do (KR)

(72) Inventors: Oui-Sik Yoo, Seoul (KR); Chan-Eol Kim, Seoul (KR)

(73) Assignee: Corentec Co., Ltd., Chungcheongnam-do (KR)

( * ) Notice: Subject to any disclaimer, the term of this patent is extended or adjusted under 35 U.S.C. 154(b) by 817 days.

(21) Appl. No.: 15/818,342

(22) Filed: Nov. 20, 2017

(65) Prior Publication Data

US 2019/0059916 A1 Feb. 28, 2019

(30) Foreign Application Priority Data

Aug. 24, 2017 (KR) .................... 10-2017-0107078

(51) Int. Cl.
*A61B 17/17* (2006.01)
*A61B 17/15* (2006.01)
(Continued)

(52) U.S. Cl.
CPC ........ *A61B 17/1764* (2013.01); *A61B 5/4585* (2013.01); *A61B 17/155* (2013.01); *A61B 17/157* (2013.01); *A61F 2/4657* (2013.01); *A61F 2/4684* (2013.01); *A61B 5/4851* (2013.01); *A61B 2017/00734* (2013.01);
(Continued)

(58) Field of Classification Search
CPC . A61B 17/155; A61B 17/157; A61B 17/1764; A61B 2562/0219; A61B 5/4585; A61B 2090/067
See application file for complete search history.

(56) References Cited

U.S. PATENT DOCUMENTS 6,022,377 A * 2/2000 Nuelle ................. A61B 17/025
606/102
6,395,005 B1 5/2002 Lovell
(Continued)

FOREIGN PATENT DOCUMENTS

JP 2006-528496 A 12/2006
JP 2015-097819 A 5/2015
(Continued)

*Primary Examiner* — Anu Ramana
(74) *Attorney, Agent, or Firm* — Workman Nydegger

(57) ABSTRACT

A smart surgical instrument for artificial joint replacement includes a femur resection device, a tibia resection device, and a detector having a shape corresponding to the resected surfaces of a femur and a tibia. The femur resection device includes a laser device such that the femur resection device can be aligned for resection of the femur without drilling an intramedullary hole, thereby preventing complications attributable to the intramedullary hole. The tibia resection device includes a laser device, thereby enabling an easy and fast surgical operation without using an extramedullary aligner used for alignment of a tibia during resection of the tibia. The detector includes a rotation detection means and a pressure detection means and is inserted between trials to allow numerical verification for medial and lateral balance of forces and a rotation state of the trials. The surgical instrument enables a precise, accurate, easy, and fast surgical operation.

22 Claims, 12 Drawing Sheets

(51) Int. Cl.
  *A61F 2/46*  (2006.01)
  *A61B 5/00*  (2006.01)
  *A61B 17/00* (2006.01)
  *A61B 90/00* (2016.01)
  *A61F 2/38*  (2006.01)

(52) U.S. Cl.
  CPC ..... *A61B 2090/067* (2016.02); *A61B 2505/05* (2013.01); *A61B 2562/0219* (2013.01); *A61B 2562/0247* (2013.01); *A61F 2/389* (2013.01); *A61F 2002/4666* (2013.01); *A61F 2002/4668* (2013.01)

(56) References Cited

U.S. PATENT DOCUMENTS

| | | | | |
|---|---|---|---|---|
| 7,837,691 | B2* | 11/2010 | Cordes | A61F 2/4684 |
| | | | | 606/88 |
| 8,118,815 | B2 | 2/2012 | van der Walt | A61B 34/10 |
| | | | | 606/102 |
| 8,882,777 | B2* | 11/2014 | Heavener | A61B 17/1764 |
| | | | | 606/87 |
| 2005/0177170 | A1 | 8/2005 | Fisher et al. | |
| 2009/0234360 | A1* | 9/2009 | Alexander | A61B 17/15 |
| | | | | 606/88 |
| 2010/0063509 | A1* | 3/2010 | Borja | A61B 17/155 |
| | | | | 606/88 |
| 2010/0087829 | A1* | 4/2010 | Metzger | A61B 17/154 |
| | | | | 606/96 |
| 2010/0198275 | A1* | 8/2010 | Chana | A61B 17/025 |
| | | | | 606/86 R |
| 2011/0213221 | A1* | 9/2011 | Roche | A61B 8/565 |
| | | | | 600/301 |
| 2013/0211411 | A1* | 8/2013 | Tuke | A61B 17/1764 |
| | | | | 606/88 |

FOREIGN PATENT DOCUMENTS

| KR | 10-2007-0085451 A | 8/2007 |
|---|---|---|
| KR | 10-1515144 B1 | 4/2015 |
| KR | 10-2015-0074396 A | 7/2015 |
| KR | 10-1612332 A | 4/2016 |

* cited by examiner

SMART SURGICAL INSTRUMENTS FOR ARTIFICIAL JOINT REPLACEMENT

CROSS REFERENCE TO RELATED APPLICATION

The present application claims priority to Korean Patent Application No. 10-2017-0107078, filed Aug. 24, 2017, the entire contents of which is incorporated herein for all purposes by this reference.

BACKGROUND OF THE INVENTION

Field of the Invention

The present invention relates generally to a smart surgical instrument for artificial joint replacement. More particularly, the present invention relates to a smart surgical instrument for artificial joint replacement, the smart surgical instrument including a femur resection device for resecting a femur, a tibia resection device for resecting a tibia, and a detector having a shape corresponding to the resected surfaces of the femur and the tibia, in which: the femur resection device includes a laser device which eliminates the need of drilling an intramedullary hole for alignment of the femur during a femur resection, thereby preventing complications; the tibia resection device includes a laser device which eliminates the need of using an extramedullary aligner for tibia resection, thereby enabling an easy and fast surgical operation; and the detector includes a rotation detection means and a pressure detection means disposed between trials, thereby enabling numerical verification for balance of forces and a rotation state of components, which enables a precise, accurate, easy, and fast surgical operation.

Description of the Related Art

The knee joint is an articulation that joins a tibia and a femur. When the knee joint cannot properly function for reasons such as being worn or damaged, it is replaced with an implant (i.e. artificial joint) through a knee replacement surgery known as knee arthroplasty.

Knee arthroplasty is a complex surgical procedure requiring a highly precise and skilled surgical technique. An implant used in the knee arthroplasty is mainly composed of a tibial component, a femoral component, and an insert being interposed between the tibial component and the femoral component and functioning like a bearing.

To implant the tibial component and the femoral component, a proximal end of a tibia and a distal end of a femur need to be resected by predetermined amounts. Since stability and mobility of the artificial knee joint depend on the inclination angles of the resected surfaces and the resection amounts of the femur and tibia, resecting the end portions of the femur and tibia needs to be highly precisely performed. Accordingly, alignment parts (cutting guide portions) need to be used to guide resection surfaces of the tibia and the femur.

The invention disclosed in Patent document discloses a guide assembly for guiding a cutting device that cuts away a distal end of a femur and a proximal end of a tibia during a knee arthroplasty. This technology uses a method of drilling deep holes in the femur and the tibia and inserting intramedullary rods (IM rods) into the holes for alignment of the femur and the tibia.

However, drilling deep holes for insertion of the IM rods as in the conventional technology may cause various complications. For example, bone cells in the holes are damaged or may be infected by bacteria, or a fat embolism in which fatty matter flows into a vein to block the flow of blood may occur due to damage of bone marrow. In addition, the drilling also requires strong force and increases the number of tools for a surgical operation, which complicates the surgical procedure and lengthens the operation time with which a surgeon is burdened.

As illustrated in FIG. 1, according to the conventional technology, a hole H is drilled in a femur 91 using a drill D so that an intramedullary rod (IM rod) can be inserted into the hole H. FIG. 2 illustrates a surgical instrument with a large knob A used to insert the intramedullary rod into the hole H. The axial alignment technique involving the drilling is disadvantageous in terms of complicated operation processes and low space utilization efficiency due to the fact that a number of surgical instruments having a large size are used.

As to resection of a tibia, as illustrated in FIG. 3, an extramedullary alignment member J extending from a proximal end 931 to a distal end 933 of a tibia is used for axial alignment of the tibia. The alignment member J has a larger volume than the tibia 93. Therefore, a surgical operation using the alignment member J is complicated and takes a long time. The complicated procedure and lengthened operation time negatively affect a patient's health and burden surgeons.

With reference to FIG. 4, after the distal end 913 of the femur and the proximal end 931 of the tibia are resected, whether the femur and the tibia are properly resected is verified with a balance checker 5'. Alternatively, after trials having the same shape as implants (prostheses) are attached to the resected surfaces, the respected surfaces are verified with the balance checker 5'. The tibia 93 is flexed or extended with respect to the femur 91 and a gap between the femur 91 and the tibia 93 is checked. As a result, the distal end 913 of the femur 91 or the proximal end 931 of the tibia 93 is further resected or the implants are replaced with new ones having a different size in accordance with the verification results.

The balance checker 5' used in the conventional technology has a problem of providing imprecise verification results because such a verification is only visually performed by eye. Therefore, the accuracy of verification results largely relies on experience and sensation of a surgeon. With reference to FIG. 4, an alignment member J' is attached to one side of the balance checker 5' for alignment of the balance checker 5'. Since the alignment member J' has a large volume and an installation time thereof is long, it is likely to burden a surgeon and to negatively affect a patient's health.

Therefore, surgical instruments for artificial joint replacement, which can easily and rapidly align cutting guide portions and have reduced sizes, are needed to enable an effective surgical operation during replacement of an artificial joint. Furthermore, the surgical instruments need to be equipped with a function of precisely and easily verifying medial and lateral force balance after resection of bones.

Document of Related Art

Patent Document

Korean Patent No. 10-1612332 (registered as of Apr. 7, 2016) "Guide Assembly For Guiding Cuts To A Femur And Tibia During A Knee Arthroplasty"

SUMMARY OF THE INVENTION

Accordingly, the present invention has been made keeping in mind the above problems occurring in the related art, and an objective of the present invention is to provide a smart surgical instrument for an artificial joint replacement, the instrument being beneficial to a patient's health and being capable of reducing a surgeon's burden by easily and rapidly aligning components of the surgical instrument by using a laser device.

Another objective of the invention is to provide a smart surgical instrument for an artificial joint replacement, the instrument being capable of preventing bone cells from being damaged or infected with bacteria and preventing complications such as a fat embolism by eliminating a process of drilling an intramedullary hole in a femur by aligning a femur resection device using a laser device.

A further objective of the invention is to provide a smart surgical instrument for an artificial joint replacement, the instrument being equipped with no additional device having a large volume because it aligns a femur resection device for resecting a femur using a laser device, thereby simplifying and speeding up a surgical operation process, which alleviates a burden to both a surgeon and a patient.

A yet further objective of the invention is to provide a smart surgical instrument for an artificial joint replacement, the instrument being equipped with two laser devices for alignment of a femur, thereby enabling easy and quick verification for alignment of a femur resection device both on a coronal plane and a sagittal plane during alignment of a femur, which alleviates a burden to a surgeon and enables a precise and accurate alignment.

A yet further objective of the invention is to provide a smart surgical instrument for an artificial joint replacement, the instrument being equipped with a rotation detection means in a femur resection device, thereby enabling numerical verification for a rotation state of a fixing portion, which alleviates a burden to a surgeon and enables an easy operation and a precise and accurate alignment.

A yet further objective of the invention is to provide a smart surgical instrument for an artificial joint replacement, the instrument aligning a tibia resection device for resection of a tibia using a laser beam, thereby improving space utilization efficiency and reducing a burden to a surgeon and a patient by not using an additional extramedullary aligner for alignment of the tibia.

A yet further objective of the invention is to provide a smart surgical instrument for an artificial joint replacement, the instrument including a tibia resection device equipped with a rotation detection means, thereby enabling precise numerical verification for an alignment state of a tibia cutting guide portion during alignment of the tibia cutting guide portion, which reduces a mental burden to a surgeon and enables an easy operation and a precise and accurate alignment.

A yet further objective of the invention is to provide a smart surgical instrument for an artificial joint replacement, the instrument including a detector having a shape corresponding to that of the resected surface of a tibia, in which the detector includes a rotation detection means, thereby providing precise numerical verification for a rotation state of an implant during alignment of the implant, which reduces a mental burden to a surgeon and enables an easy operation and a precise and accurate alignment.

A yet further objective of the invention is to provide a smart surgical instrument for an artificial joint replacement, the instrument including a detector equipped with a pressure detection means, thereby enabling precise numerical verification for medial and lateral balance and pressure distribution of an implant, which reduces a burden to a surgeon and enables an easy operation and a precise and accurate alignment.

A yet further objective of the invention is to provide a smart surgical instrument for an artificial joint replacement, the instrument including a detector having a knob means so that the detector can be easily installed and removed by holding the knob means.

A yet further objective of the invention is to provide a smart surgical instrument for an artificial joint replacement, the instrument including a balance checker mounted with a detector, in which the balance checker includes a laser device which enables verification for axial alignment with a laser beam during balance checking, which enables a fast and easy operation.

A yet further objective of the invention is to provide a smart surgical instrument for an artificial joint replacement, the instrument charging a battery of a detector in an wireless manner, thereby enabling an easy, simple, and fast operation.

A yet further objective of the invention is to provide a smart surgical instrument for an artificial joint replacement, the instrument having a structure in which a battery and a detector are detachably combined with each other so that the battery can be conveniently charged.

In order to accomplish the above object, the present invention is implemented by embodiments having the structures described below.

According to one embodiment of the present invention, there is provided a smart surgical instrument for an artificial joint replacement, the surgical instrument including a laser device, thereby easily and conveniently performing alignment of components thereof by using the laser device.

According to another embodiment of the present invention, the surgical instrument may further include a femur resection device for resecting a femur, wherein the femur resection device includes a laser device, thereby eliminating a process of drilling an intramedullary hole for alignment of the femur during resection of the femur, thereby preventing complications attributable to drilling the intramedullary hole.

According to a further embodiment of the present invention, the femur resection device may include: a fixing portion attached to a distal end of the femur; a cutting guide portion aligned with respect to the fixing portion; and a connecting portion connected to one side of the fixing portion, in which the connecting portion comprises a laser device aligning the fixing portion using a laser beam emitted by the laser device, thereby enabling an easy and convenient surgical operation.

According to a yet further embodiment of the present invention, the connecting portion may include an ML laser device emitting a laser beam toward a proximal end of the femur from a front side of the femur and an AP laser device emitting a laser beam toward the proximal end of the femur from a medial side or a lateral side of the femur, thereby facilitating alignment of the fixing portion in a medial-lateral direction and a an anterior-posterior direction.

According to a yet further embodiment of the present invention, the connecting portion may include an ML member extending in the medial-lateral direction and an AP member extending in the anterior-posterior direction, and the ML member and the AP member respectively include the ML laser device and the AP laser device, thereby facilitating alignment of the fixing portion in the medial-lateral direction and the anterior-posterior direction.

According to a yet further embodiment of the present invention, the cutting guide portion may include a frontal cutting guide portion that guides cutting of a frontal portion of the distal end of the femur and a distal cutting guide portion that guides cutting of a middle portion of the distal end of the femur, and the distal cutting guide portion may be aligned by being connected to the fixing portion via the frontal cutting guide portion.

According to a yet further embodiment of the present invention, the fixing portion may include a rotation detection means that enables numerical verification for a rotation state of the fixing portion during alignment of the fixing portion, which is performed by using a laser beam, thereby facilitating precise, accurate, and fast alignment of the fixing portion and enabling an accurate surgical operation by preventing the fixing portion from being displaced after the fixing portion is aligned.

According to a yet further embodiment of the present invention, the rotation detection means may be a gyro sensor.

According to a yet further embodiment of the present invention, the surgical instrument may further include a tibia resection device for resecting a tibia, in which the tibia resection device includes a laser device, whereby the surgical instrument enables an easy and fast surgical operation by eliminating the need of using an extramedullary aligner during alignment of the tibia for resection of the tibia According to a yet further embodiment of the present invention, in the surgical instrument, the tibia resection device may include a tibia cutting guide portion attached to a frontal end of the tibia and a connector combined with the tibia cutting guide portion, and the connector may include a laser device emitting a laser beam to a distal end of the tibia, whereby the surgical instrument facilitates alignment of the tibia cutting guide portion.

According to a yet further embodiment of the present invention, in the surgical instrument, the tibia cutting guide portion may include a rotation detection means, thereby enabling numerical verification for an alignment state of the tibia cutting guide portion when the tibia cutting guide portion is aligned with a laser beam, whereby the surgical instrument enables precise, accurate, easy, and fast alignment of the tibia cutting guide portion.

According to a yet further embodiment of the present invention, there is provide a surgical instrument for artificial joint replacement, the surgical instrument including a rotation detection means, thereby enabling a precise, accurate, and easy surgical operation by numerically precisely controlling a resection position of a bone and an installation position of an implant.

According to a yet further embodiment of the present invention, the surgical instrument may further include: a reference rotation detection means providing a reference position used to detect a rotation angle of a component of the surgical instrument; and an operation rotation detection means detecting the rotation angle of the component with respect to the reference rotation detection means.

According to a yet further embodiment of the present invention, the surgical instrument may further include a detector having a shape corresponding to a tibial component trial and a resected surface of the tibia, in which the detector includes an operation rotation detection means and a pressure detection means and is inserted between the tibial component trial and an insert trial, thereby enabling an easy and fast surgical operation by allowing numeral verification for medial and lateral balance and for a rotation degree of the trials.

According to a yet further embodiment of the present invention, the detector may be provided with a positioning recess in one surface thereof, and the tibial component trial may be provided with a positioning protrusion at one surface thereof to position the detector, in which the detector has the positioning recess at a position corresponding to the positioning protrusion so that the detector is promptly and easily positioned on the tibial component trial and is prevented from slipping after being placed on the tibial component trial.

According to a yet further embodiment of the present invention, the surgical instrument may include a femoral component trial and a balance checker inserted between the tibia and the femur to check medial and lateral balance, in which the balance checker includes a detector having the a shape corresponding to the resected surface of the tibia, and the detector includes an operation rotation detection means and a pressure detection means to allow numerical verification for medial and lateral balance and a rotation state when the balance checker is inserted between the tibia and the femur, thereby enabling an easy and fast surgical operation.

According to a yet further embodiment of the present invention, the balance checker may include a first insertion portion provided with an accommodation recess in which the detector is accommodated, the detector may be provided with a knob means at a periphery portion thereof, and the accommodation recess may be provided with an outer recess at a position corresponding to the knob means such that the detector is easily removable from the balance checker.

According to a yet further embodiment of the present invention, the balance checker may include a second insertion portion composed of an upper plate and a lower plate such that the detector is inserted between the upper plate and the lower plate, whereby the detector is inserted into and removed from the balance checker in a sliding manner.

According to a yet further embodiment of the present invention, the balance checker may be equipped with a laser device at one side thereof, thereby allowing easy verification for an alignment state of the balance checker.

According to a yet further embodiment of the present invention, the detector may be equipped with a battery for supplying power to operate the operation rotation detection means and the pressure detection means, and the battery may be charged through a wireless charging method.

According to a yet further embodiment of the present invention, the battery may be detachably mounted in the detector.

According to the present invention, it is possible to obtain advantages described below due to the preferred embodiments, the structures to be described below, and combinations and applications of the embodiments or structures.

According to the present invention, since a surgical instrument includes a laser device, it is possible to easily and promptly align components of the instrument, thereby reducing a burden to a surgeon and providing effects advantageous for recovery of a patient.

According to the present invention, since the surgical instrument aligns a femur resection device for resecting a femur with a laser beam, it is not necessary to drill an intramedullary hole in the femur, thereby preventing bone cells from being damaged and thereby minimizing complications such as infection or a fat embolism.

According to the present invention, since the surgical instrument aligns a femur resection device for resecting a femur with a laser beam, it is not necessary to use additional devices having large sizes. Therefore, an operation process is simplified and sped up, which is advantageous for recovery of a patient and reduces a burden to a surgeon.

According to the present invention, since the surgical instrument uses two laser devices during alignment of a femur, a coronal plane alignment and a sagittal plane alignment can be easily and promptly performed. Therefore, a burden to a surgeon is reduced, and a precise and accurate alignment is possible.

In addition, since the femur resection device includes a rotation detection means, the rotation state of a fixing portion can be verified with a specific numerical value, which reduces a burden to a surgeon, facilitates a surgical operation, and enables an easy, precise, and accurate alignment.

In addition, since a tibia resection device for resecting a tibia is aligned with a laser beam, it is not necessary to use an additional extramedullary aligner, which improves space utilization efficiency and speeds up a surgical operation, thereby reducing a burden to a surgeon and being advantageous for recovery of a patient.

In addition, since the tibia resection device includes a rotation detection means that enables numerical verification for an alignment state of the tibia resection device, a burden to a surgeon is reduced, a surgical operation is facilitated, and a precise and accurate alignment is possible.

In addition, the surgical instrument includes a detector having a shape corresponding to that of the resected surface of the tibia, and the detector includes a rotation detection means. Therefore, a rotation state of an implant can be precisely verified with a specific numerical value during alignment of an implant. Thus, a burden to a surgeon is reduced, a surgical operation is facilitated, and a precise and accurate alignment is possible.

In addition, the detector includes a pressure detection means. Therefore, medial and lateral force balance and pressure distribution can be precisely verified with specific numerical values. Thus, a burden to a surgeon is reduced, a surgical operation is facilitated, and a precise and accurate alignment is possible.

In addition, the detector has a knob means to be held for movement. Therefore, the detector can be easily installed and removed by holding the knob means.

In addition, the surgical instrument includes a balance checker in which the detector is accommodated, and the balance checker includes a laser device. Therefore, axial alignment of an implant is verified during verification for balance using a laser beam, which enables an easy and fast surgical operation.

In addition, since a battery in the detector can be charged in a wireless charging manner, an operation can be conveniently performed in a short time.

In addition, since the battery is detachably mounted in the detector, the battery can be conveniently charged.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Figure 1:
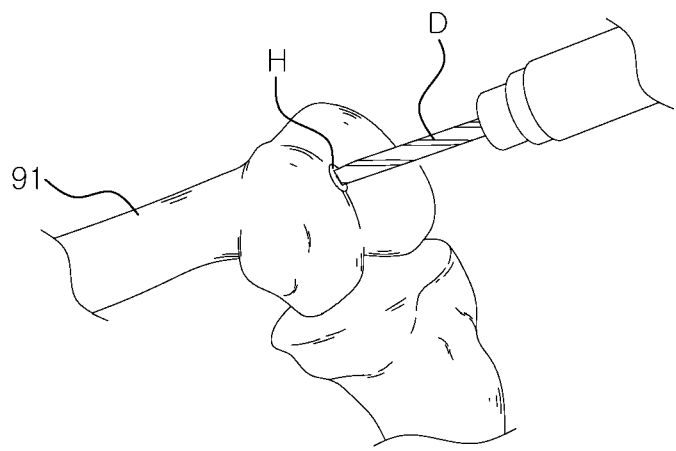
FIG. 1 is a perspective view illustrating a state in which a hole is drilled in a femur such that an intramedullary rod (IM rod) can be inserted into the hole of the femur, according to a conventional art.
Figure 2:
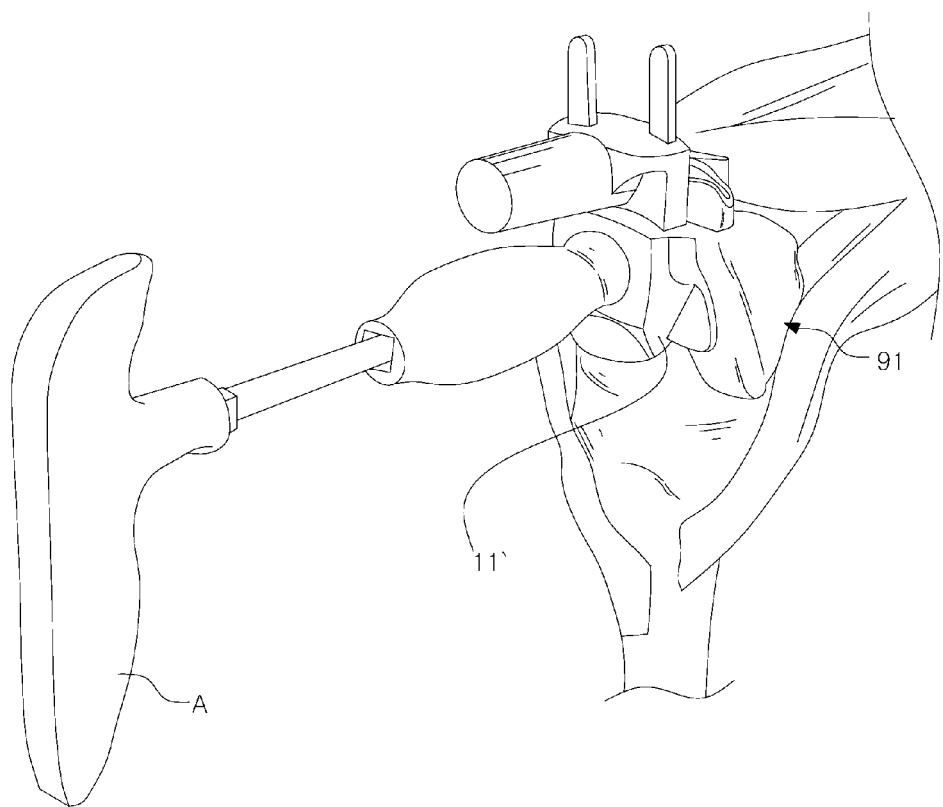
FIG. 2 is a perspective view illustrating a state in which various components of a surgical instrument are arranged to resect a portion of the femur after the intramedullary rod is inserted into the hole of the femur, according to the conventional art.
Figure 3:
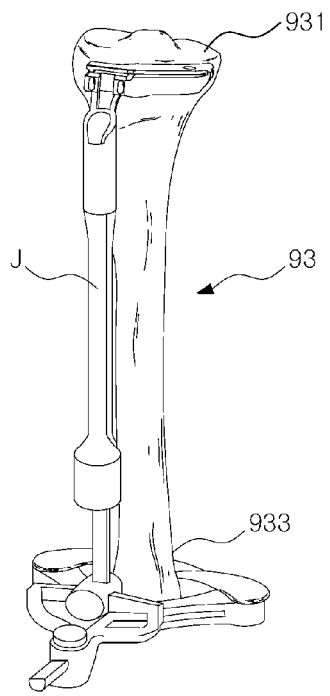
FIG. 3 is a side view illustrating a state in which a cutting guide portion is aligned using an extramedullary alignment member to resect a portion of a tibia, according to the conventional art.
Figure 4:
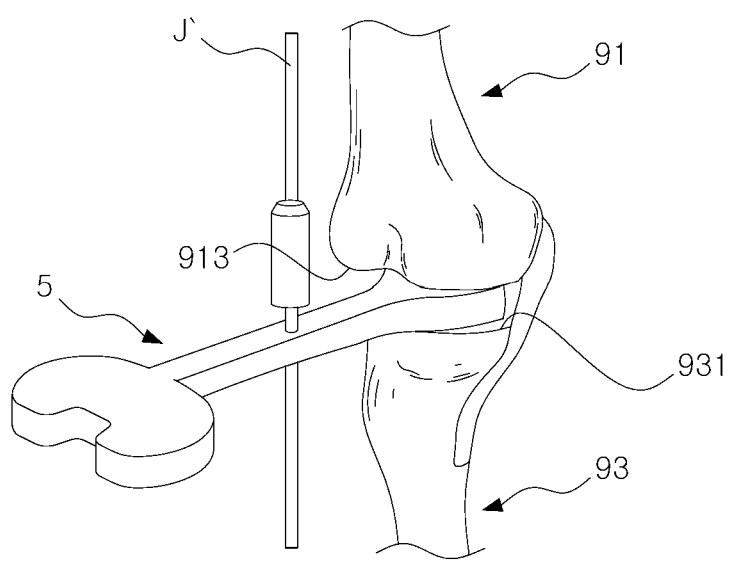
FIG. 4 is a side view illustrating a state in which axial alignment is verified using an additional alignment member during verification of balance which is performed with a balance checker, according to the conventional art.

Hereinbelow, a surgical instrument for artificial joint replacement according to the present invention will be described with reference to the accompanying drawings. Like reference numbers refer to like elements throughout the drawings. Detailed descriptions of known functions and configurations which have been deemed to obscure the gist of the present invention will be omitted below. Unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Next, a surgical instrument for artificial joint replacement will be described in detail with reference to the accompanying drawings.

With reference to FIGS. 6, 11, 12, and 17, according to one embodiment of the present invention, a surgical instrument S includes a femur resection device 1, a tibia resection device 3, a detector 8, a balance checker 5, and a trial 7.

Figure 5:
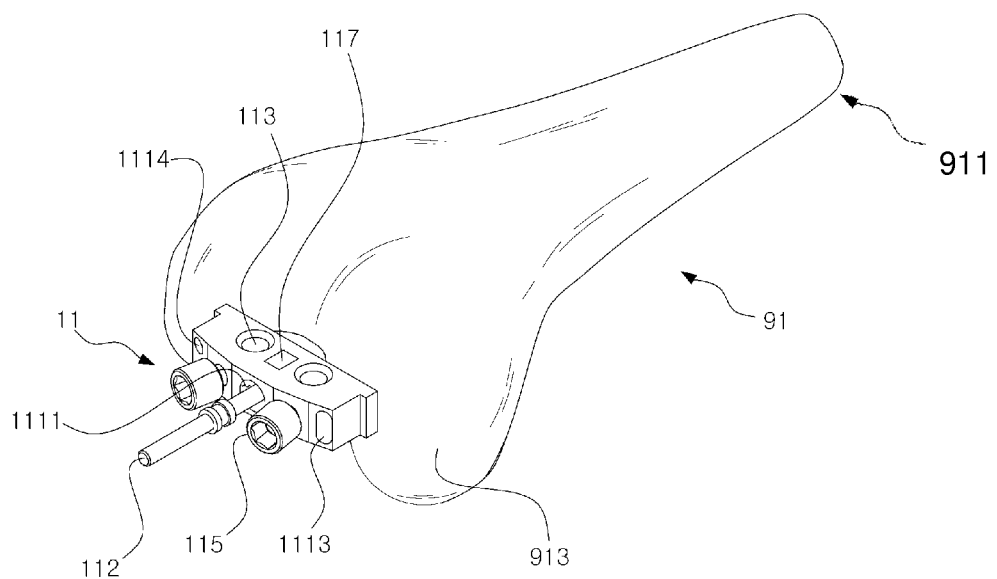
FIG. 5 is a perspective view illustrating a state in which a fixing portion is attached to a femur, according to one embodiment of the present invention.
Figure 6:
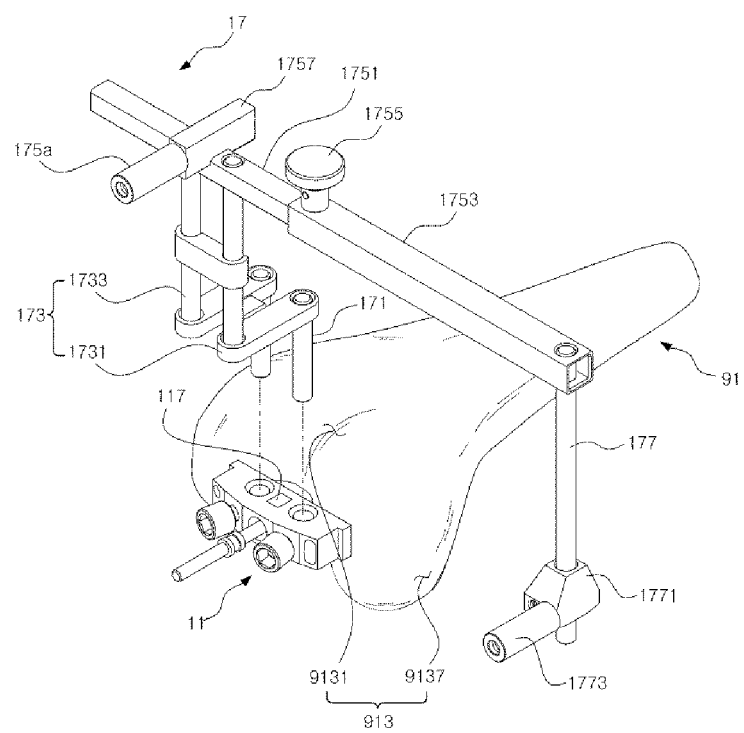
FIG. 6 is a perspective view illustrating principles of connecting a connecting portion to the fixing portion according to one embodiment of the present invention.
Figure 9:
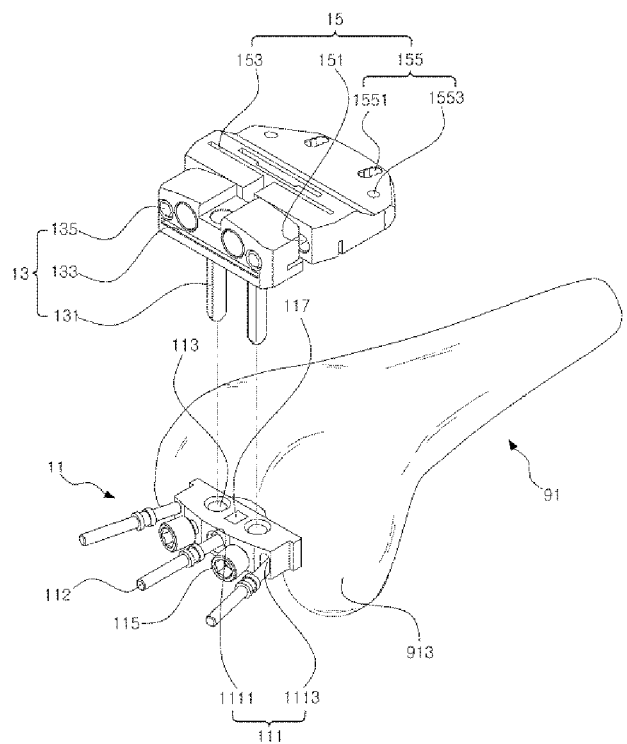
FIG. 9 is a perspective view illustrating a process of combining a cutting guide portion with the fixing portion according to one embodiment of the present invention.

With reference to FIGS. 5, 6, and 9, the femur resection device 1 includes a fixing portion 11 attached to a distal end 913 of a femur 91, a connecting portion connected to the fixing portion 11, a frontal cutting guide portion 13 connected to the fixing portion 11, and a distal cutting guide portion 15 connected to the frontal cutting guide portion 13.

With reference to FIG. 5, the fixing portion 11 which is a component for aligning the cutting guide portions 13 and 15 with respect the femur 91 is attached to the distal end 913 of the femur 91. The fixing portion 11 includes a distal fixation hole 111 to be engaged with the distal end 913 of the femur 91, a first connection hole 113 to be engaged with the frontal cutting guide portion 13 and the connecting portion 17, a first locking means 115 for locking a member inserted into the first connection hole 113, and a fixing portion rotation detection means 117 for detecting a rotation state of the fixing portion 11.

The distal fixation hole 111 is a hole through which a fixing portion fixing means 112 used to attach the fixing portion 11 to the distal end 913 of the femur 91 is inserted. The distal fixation hole 11 is composed of a distal center fixation hole 1111 disposed at a center portion of the fixing portion, a distal lopsided elongated hole 1113 disposed at one side of the fixing portion and elongated in a vertical direction, and a distal lopsided fixation hole 1114 disposed at the opposite side of the distal lopsided elongated hole 1113 and having a circular shape.

The first connection hole 113 is a hole extending through the fixing portion 11 in an anterior-posterior direction. A first connection member 131 of the frontal cutting guide portion 13 or a connection member 173 of the connecting portion 17 is selectively inserted into the first connection hole 113. The first locking means 115 is a component for securely fixing the first connection member 131 or the connection member 173 inserted into the first connection hole 113 in a screw-locking manner.

The fixing portion rotation detection means 117 is structured to detect a numerical value of the axial alignment state when the fixing portion 11 is attached to the distal end 913 of the femur 91. The fixing portion rotation detection means 117 may be a sensor that detects a rotation angle by measuring an angular speed or an angular acceleration. Preferably, the fixing portion rotation detection means 117 may be a gyro sensor. Since the rotation state of the fixing portion 11 is detected by the rotation detection means 117, when the fixing portion 11 is aligned using laser devices (denoted by reference numbers 1759 and 1773 in FIG. 6), which will be described below, it is possible to verify the rotation state of the fixing portion 11 with a numerical value during alignment of the fixing portion 11. Therefore, a precise and accurate alignment is possible, which reduces a surgeon's stress. In addition, it is possible to detect a displacement of the fixing portion 11 after the alignment of the fixing portion 11 is performed once. Therefore, a precise and accurate resection of the femur is possible. The fixing portion rotation detection means 117 needs to detect a rotation angle of the fixing portion with respect to the femur 91. Therefore, it is preferable that an additional rotation detection means is installed on the femur 91.

The rotation detection means 117 may further include a communication device to send the rotation state of the fixing portion 11 to an external display device. Therefore, the rotation state of the fixing portion 11 can be verified using the external display device. The fixing portion 11 is a small device. Therefore, it is difficult for a surgeon to precisely observe the state of the fixing portion 11 when it is installed on a small surgical area. For this reason, when the fixing portion 11 communicates with the external display device, the surgeon can clearly observe the rotation state of the fixing portion 11 due to an enlarged image or numerical information displayed on the external display device. Therefore, the surgeon can easily, precisely, and accurately align the fixing portion with respect to the femur.

With reference to FIG. 6, the connecting portion 17 is a component used to connect a laser device to the fixing portion for fast and easy alignment of the fixing portion 11. The connecting portion 17 includes a connection hole insertion member 171 to be inserted into the first connection hole 113, the connection member 173 extending from one side of the connection hole insertion member 171 at a predetermined angle, an ML member 175 connected to the connection member 173 and extending in a medial-lateral direction, and an AP member 177 connected to a portion of the ML member 175 and extending in the anterior-posterior direction.

The connection hole insertion member 171 is a component that is inserted into the first connection hole 113 of the fixing portion 11 to securely fix the connecting portion 17 at a predetermined position. Preferably, there are two connection hole insertion members 171, thereby preventing the connecting portion 17 connected to the fixing portion 11 from being axially rotated.

The connection member 173 is a component that connects the connection hole insertion member 171 and the ML member 175 to each other. The connection member 173 includes a first connection member 1731 extending in a proximal-distal direction of the femur 91 and a second connection member 1773 extending from an end of the first connection member 1731 in the anterior-posterior direction. There are also two connection members 173 each including the first connection member 1731 and the second connection member 1733 like the connection hole insertion members 171.

The ML member 175 extends from an end of the connection member 173 in the medial-lateral direction. The ML member 175 includes an ML member connection means 1757 and an ML laser device 1759 combined with the ML member connection means 1757.

Figure 8:
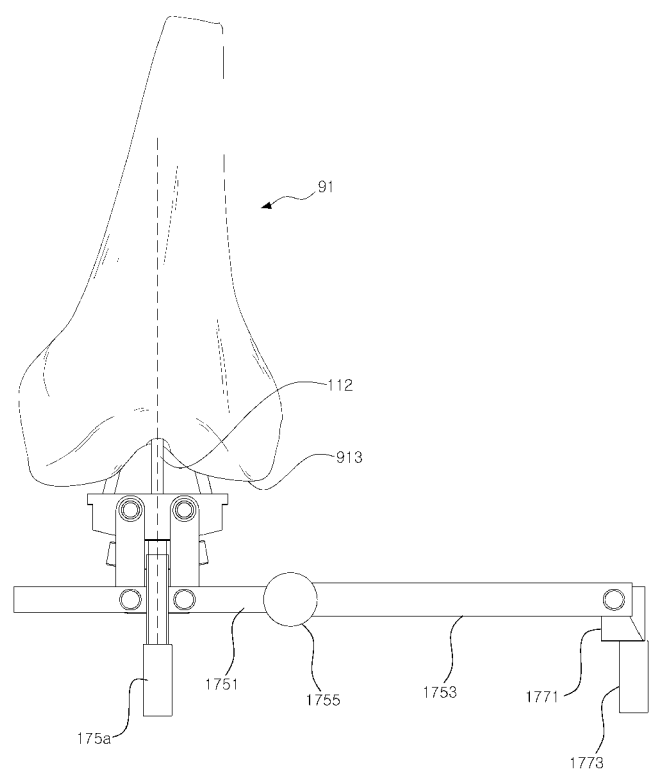
FIG. 8 is a front view illustrating the process of aligning the axis of the femur using the laser beam according to one embodiment of the present invention.

The ML laser device 1759 emits a laser beam in a direction from a front side 9131 of the distal end 913 of the femur 91 to the proximal end 911 of the femur 91, to help the fixing portion 11 to be fixed at a correct position. The laser beam travels along the front surface of the femur 91, thereby preventing the fixing portion 11 from deviating, in a medial direction or a lateral direction, from the mechanical axis of the femur 91 and from being fixed in a misaligned state. The principles of the alignment are shown in FIG. 8 in detail. With reference to FIG. 8, alignment between the laser beam and the mechanical axis of the femur 91 on the coronal plane can be easily verified.

The AP member 177 extends from an end of the ML member 175 in the anterior-posterior direction. The AP member 177 may include an AP member connection means 1771 and an AP laser device 1773 combined with the AP member connection means 1771.

Figure 7:
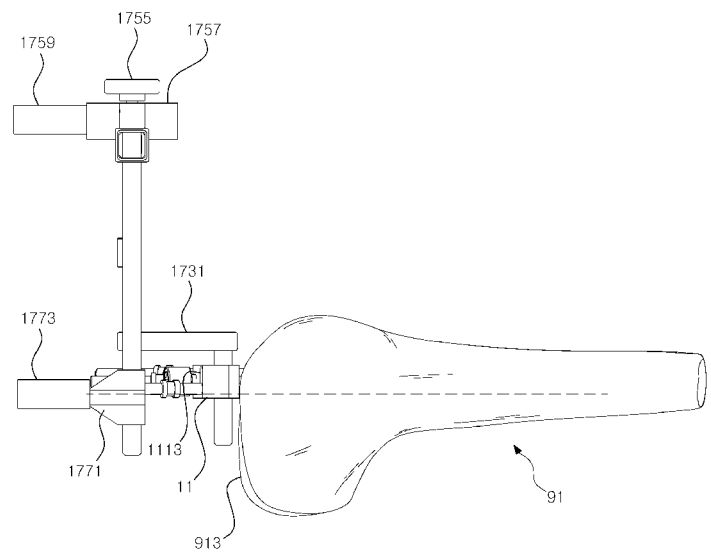
FIG. 7 is a side view illustrating a process of aligning the axis of a femur using a laser beam according to one embodiment of the present invention.

The AP laser device 1773 emits a laser beam in a direction from one side surface of the distal end 913 of the femur 91 to the proximal end 911 of the femur 91, thereby helping the fixing portion 11 to be fixed at a correct position. The laser beam travels along one side surface of the femur 91, thereby preventing the fixing portion 11 from deviating in an anterior direction or a posterior direction, from the axis of the femur 91. The principles of the alignment are shown in FIG. 7. With reference to FIG. 7, since the laser beam travels along one side of the femur 91, it is possible to easily verify the alignment of the fixing portion with respect to the femur 91 on the sagittal plane.

With reference to FIG. 9, the frontal cutting guide portion 13 is a component that guides cutting of the frontal end of the femur 91 and is fixed to the fixing portion 11 that is attached to the distal end 913 of the femur 91 after being aligned with respect to the fixing portion by using the ML laser and the AP laser. The frontal cutting guide portion 13 includes the first connection member 131 to be inserted into the first connection hole 113, a frontal cutting guide slot 133 for guiding cutting of the frontal end, and a second connection member 135 that guides a position of a cutting saw within the frontal cutting guide slot 133.

The first connection member 131 is inserted into the first connection hole 113, thereby aligning and fixing the frontal cutting guide portion 13 with the fixing portion 11 and at a correct position. There may be two first connection members 131 to prevent axial rotation of the frontal cutting guide portion 13.

The frontal cutting guide slot 133 is an elongated hole in which a cutting device such as a cutting saw moves, thereby guiding the cutting device that cuts away a front portion of the femur.

The second connection member 135 extends in the direction from the distal end to the proximal end of the femur 91, and is inserted into a first connection recess 151 of the distal cutting guide portion 15 described below. The second connection member 135 connects the distal cutting guide portion 15 to the fixing portion 11 that is preliminarily aligned by using a laser beam, thereby aligning the distal cutting guide portion 15.

The distal cutting guide portion 15 is a component that guides cutting of the distal end 913 of the femur and is combined with the frontal cutting guide portion 13. The distal cutting guide portion 15 includes the first connection recess 151, a distal cutting guide slot 153, and a frontal fixation hole 155.

The first connection recess 151 is an element into which the second connection member 135 is inserted such that the distal cutting guide portion 15 is automatically positioned at a correct position.

The distal cutting guide slot 153 is also an elongated hole in which a cutting device such as a cutting saw moves to cut away a distal portion of the femur 91, like the frontal cutting guide slot 133.

The frontal fixation hole 155 is an element used to fix the distal cutting guide 15 to the frontal end of the tibia 93, and includes a frontal center fixation hole 1551 and a frontal inclined fixation hole 1553.

The frontal center fixation hole 1551 is a portion into which a pin used to fix the distal cutting guide portion 15 that is properly aligned is inserted before the frontal cutting guide portion 13, which is connected to the fixing portion to resect the distal end 913 of the femur 91, is removed. The frontal inclined fixation hole 1553 is an oblique hole inclined with respect to the anterior-posterior direction to securely fix the distal cutting guide portion 15 at a specific position of the tibia 93 such that cutting of the tibia 93 is guided by the distal cutting guide portion 15. In order to securely fix the distal cutting guide portion 15 from which the frontal cutting guide portion 13 is removed to the front surface of the tibia 93, three or more pins need to be inserted into the fixation holes including the frontal center fixation hole and the frontal inclined fixation hole 1553.

Figure 10:
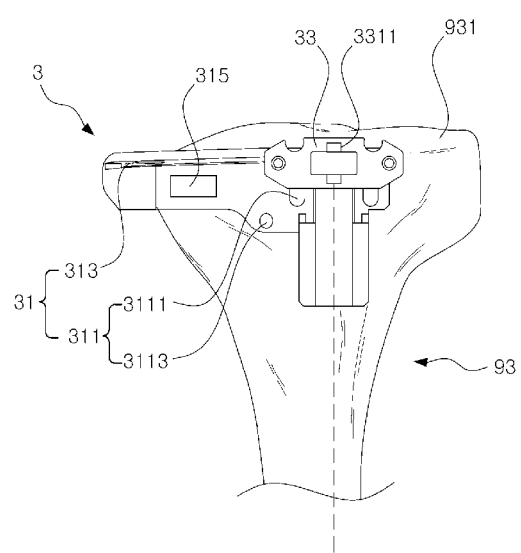
FIG. 10 is a front view illustrating a process of attaching a tibia resection device to a tibia and aligning the tibia resection device with the axis of the tibia using a laser beam according to one embodiment of the present invention.
Figure 11:
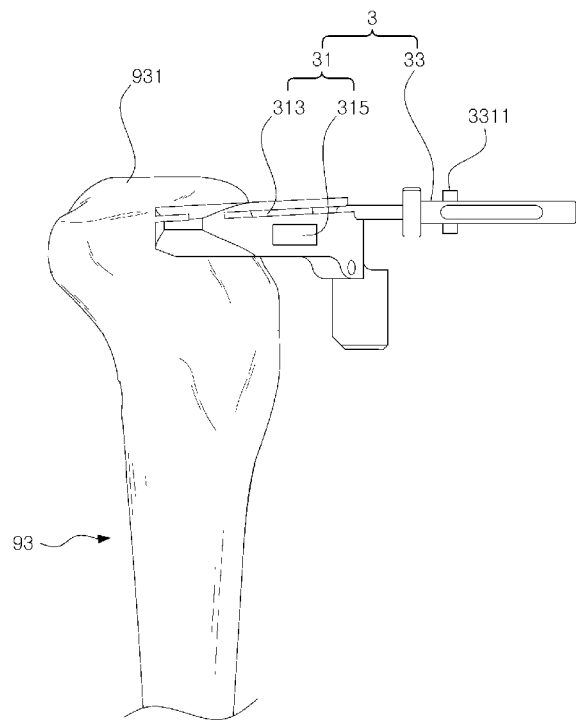
FIG. 11 is a side view illustrating a side view illustrating the process of attaching the tibia resection device to the tibia and aligning the tibia resection device with the axis of the tibia using the laser beam according to one embodiment of the present invention.
Figure 12:
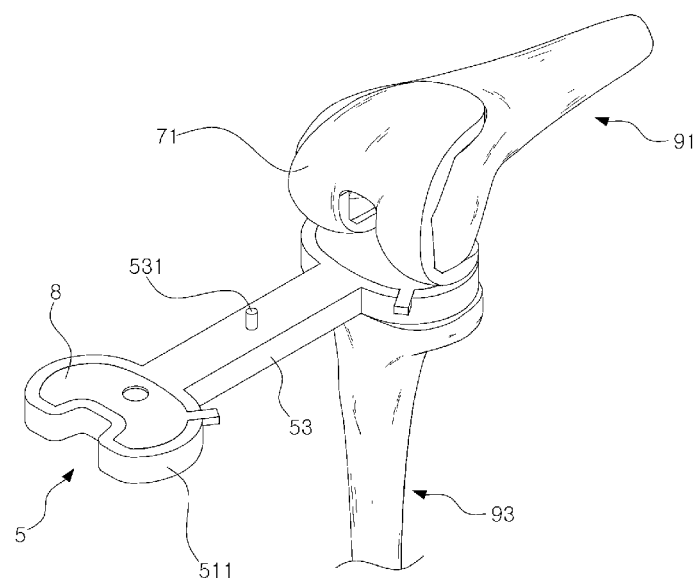
FIG. 12 is a side view illustrating a state in which the balance checker according to one embodiment of the present invention is inserted and the knee joint is flexed.

With reference to FIGS. 10 and 11, the tibia resection device 3 includes the tibia cutting guide portion 31 attached to the frontal end of the tibia 93 and a connector 33 attached to the tibia cutting guide portion 31.

The tibia cutting guide portion 31 is a component that guides cutting of the proximal end 931 of the tibia 93. The tibia cutting guide portion 31 includes a tibia fixation hole 311 used to fix the tibia cutting guide portion 31 to the tibia 93, a tibia cutting guide slot 313, and a guide portion rotation detection means 315.

The tibia fixation hole 311 is a hole provided to fix the tibia cutting guide portion 31 to the tibia 93, and the tibia cutting guide portion 31 preferably includes three or more tibia fixation holes 311.

Similarly with the frontal cutting guide slot 133, the tibia cutting guide slot 313 is an elongated hole in which a cutting device, such as a cutting saw, to resect the proximal end 931 of the tibia 93 is inserted to move in a predetermined direction.

The guide portion rotation detection means 315 is a component to measure a numerical value of an axial alignment state when the tibia cutting guide portion 31 is fixed to the proximal end 931 of the tibia 93. Preferably, the guide portion rotation detection means 315 is a gyro sensor. The detection means 315 may further include a communication device to communicate with an external display device so that a specific numerical value of the rotation state of the tibia cutting guide portion 31 can be checked from the external display device. When performing knee joint replacement, since a surgical area is small, it is difficult for a surgeon to clearly observe the surgical area. However, when the surgical area is displayed on the external display device, a surgeon can clearly and precisely observe and check the rotation state of the tibia cutting guide portion and can easily and accurately align the cutting guide portion with a less burden. Due to the rotation detection means described above, when the tibia cutting guide portion 31 is aligned using a laser and rotated for alignment, numerical verification is possible. Furthermore, during the resection of the tibia following the alignment and fixation of the cutting guide portion, it is possible to detect rotation or twisting of the tibia cutting guide portion 31, thereby enabling an accurate resection. Since the guide portion rotation detection means 315 needs to detect a relative rotation angle of the cutting guide portion with respect to the tibia 93, an additional rotation detection means is preferably installed on the tibia 93.

The connector 33 is combined with the tibia cutting guide portion 31 and is equipped with a tibia laser device 3311 on one side surface thereof.

The tibia laser device 3311 assists a surgeon in positioning the tibia cutting guide portion 31 at a correct position when fixing the tibia cutting guide portion 31 to the tibia 93. With reference to FIG. 11, the tibia laser device 3311 is installed in front of the tibia 93 and emits a laser beam toward the distal end 933 from the proximal end 931. Accordingly, the tibia laser device 3311 prevents the tibia cutting guide portion 31 from rotating in a medial direction or a lateral direction on the coronal plane and from being fixed at a wrong position. The principles of this alignment are shown in FIG. 10. With reference to FIG. 10, a surgeon rotates the tibia cutting guide portion 31 in the medial direction or the lateral direction while checking whether a travel direction of a laser beam is coincident with the axis of the tibia 93 until axis of the tibia becomes coincident with the travel direction of the laser beam. In this way, the tibia cutting guide portion is properly aligned. Therefore, an axial alignment process is easily performed in a short time, thereby reducing a burden to a surgeon, shortening an overall operation time, and helping recovery of a patient.

Figure 14:
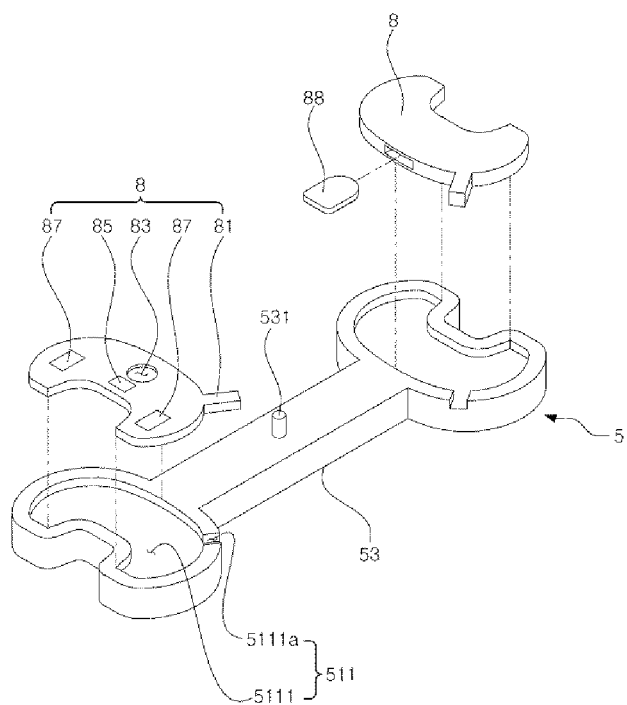
FIG. 14 is an exploded perspective view illustrating the balance checker and a detector according to one embodiment of the present invention.

With reference to FIG. 14, the detector 8 is inserted between the distal end 913 of the femur 91 and the proximal end 931 of the tibia 93 to detect a rotation angle of an implant and a pressure applied to the implant. The detector 8 is a thin plate having a shape similar to or the same as that of the resected surface of the tibia 93. The detector 8 is provided with a knob means 81, a positioning recess 83, an operation rotation detection means 85, a pressure detection means 87, and a battery 88.

Figure 16:
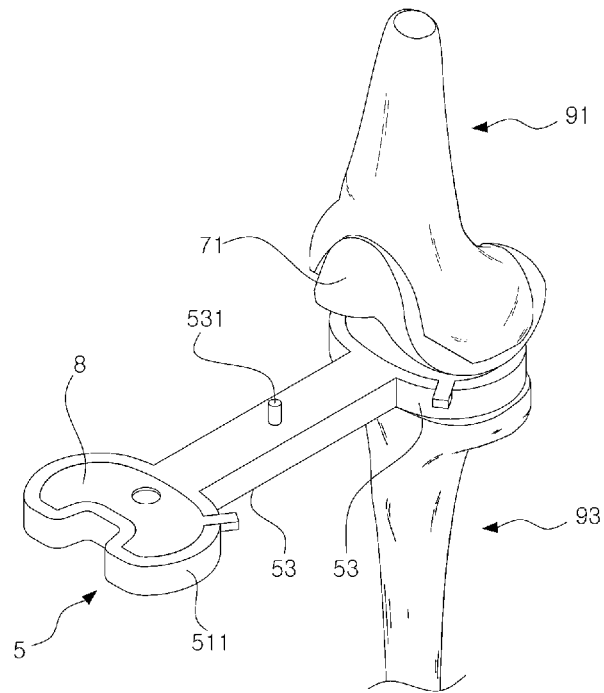
FIG. 16 is an exploded perspective view illustrating a trial and the detector according to one embodiment of the present invention.
Figure 17:
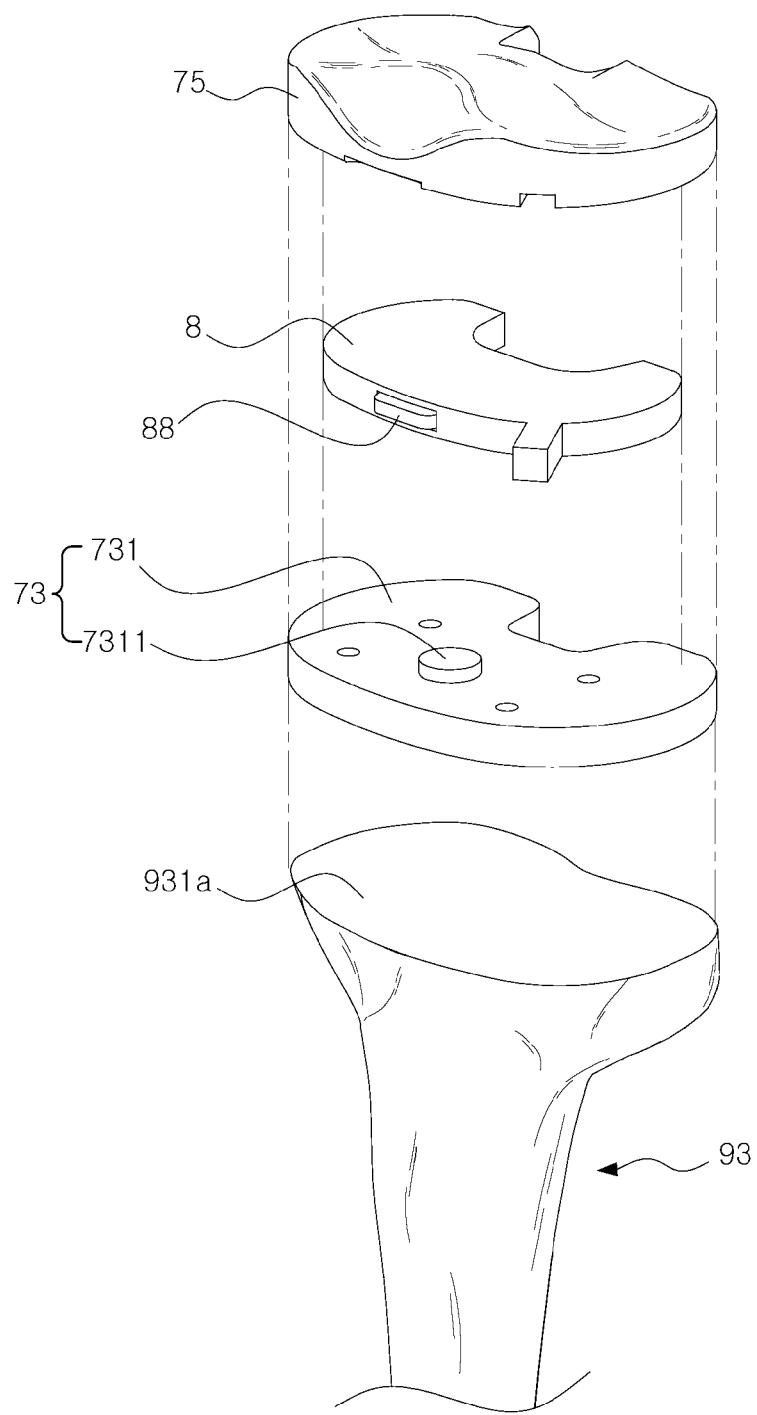
FIG. 17 is an exploded perspective view illustrating an insert trial and the detector according to one embodiment of the present invention.
Figure 18:
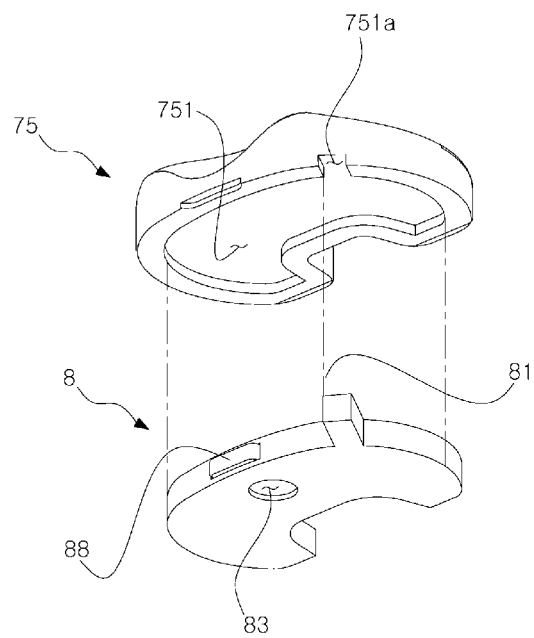
FIG. 18 is a bottom exploded perspective view illustrating the trial and the detector according to one embodiment of the present invention.
Figure 19:
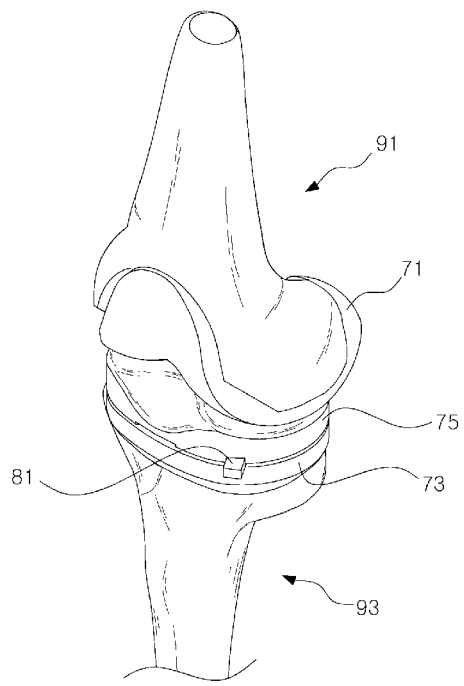
FIG. 19 is a perspective view illustrating a process of verifying balance using the trial and the detector in a state in a knee joint is extended, according to one embodiment of the present invention.
Figure 20:
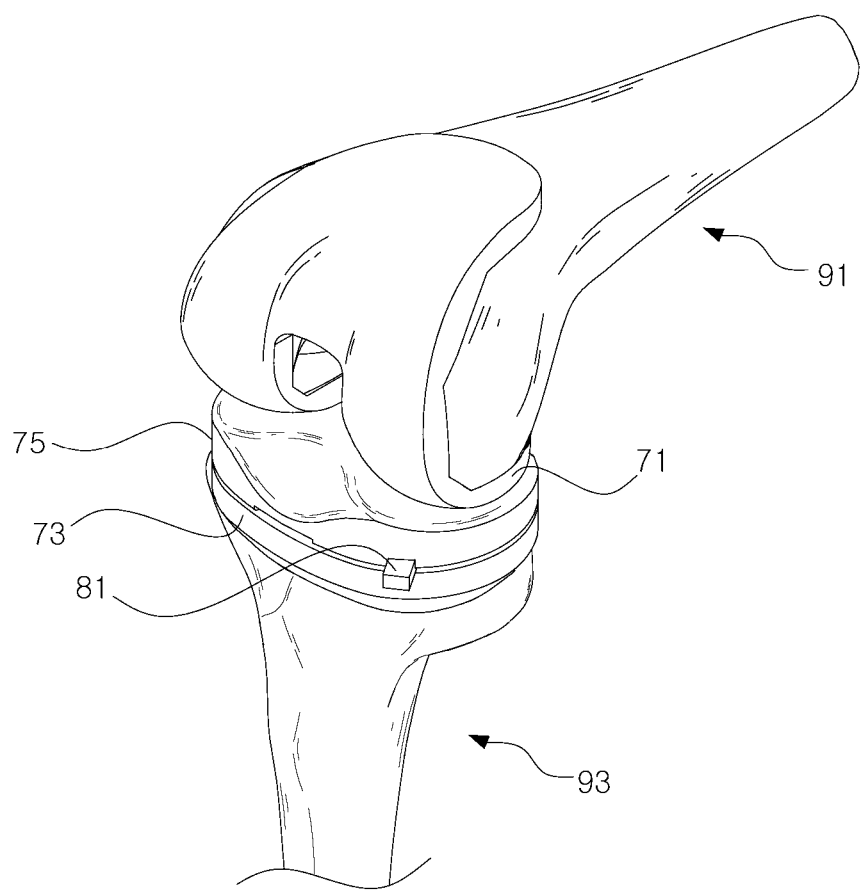
FIG. 20 is a perspective view illustrating a process of verifying balance using the trial and the detector in a state in which a knee joint is flexed, according to one embodiment of the present invention.

The knob means 81 is formed at the outer periphery of the detector 8. Since the knob means 81 is formed to protrude from the outer periphery of the detector 8, the detector 8 can be conveniently moved by holding the knob means 81 when the detector 8 is mounted on and removed from the balance checker (refer to reference number 5 in FIG. 16) or a tibial component trial (refer to reference number 73 in FIG. 17).

The positioning recess 83 is a recessed portion having a predetermined depth and is provided in one surface of the detector 8. Preferably, the positioning recess 83 is formed in a center portion of a lower surface of the detector 8. The positioning recess 83 is engaged with a positioning protrusion 7311 (described below) of the tibial component trial 83, thereby preventing the detector 8 from escaping when verifying the rotation and pressure of trials 7.

The operation rotation detection means 85 provided in or on one surface of the detector 8 detects a rotation state of the trial 7 and provides a numerical value of the rotation state. Preferably, the operation rotation detection means 85 is a gyro sensor and is equipped with a communication device so that the numerical value of the rotation state of the trial 7 can be checked using an external display device. A surgical area in an actual knee joint replacement operation is very small, so it is difficult for a surgeon to clearly verify the rotation state of the trial with eye. Therefore, the external display device is connected to the detector 85 to clearly show the rotation state of the trial. Therefore, a surgeon can easily perform an alignment between the bones and the surgical instrument with a less burden.

In addition, since the operation rotation detection means 85 needs to detect a relative rotation state of components of the surgical instrument with respect to the tibia 93 or the femur 91, the tibia 93 or the tibial component trial 73 is mounted with a reference rotation detection means serving as a reference position for detecting a rotation angle. Alternatively, the reference rotation detection means may be mounted on the femur 91 or the femoral component trial 71. Further alternatively, both the tibia (or the tibial component trial) and the femur (or the femoral component trial) may be provided with respective reference rotation detection means. This will be described in more detail below.

When the detector 8 is inserted between the femur 91 and the 93, the pressure detection means 87 detects the force per unit area applied to the femur 91 and the tibia 93 to obtain medial and lateral force balance. The pressure detection means may be a piezoelectric element using a piezoelectric effect, a strain gauge, a load cell, or the like. In this case, preferably, the detector may include a communication device to communicate with an external display device, thereby enabling a surgeon to verify the pressure distribution using the external display device, in the form of numerical numbers. Therefore, unlike a conventional art in which the medial and lateral force balance and the pressure distribution are checked depending on a surgeon's experience and sensation, according to the present invention, a surgeon can precisely verify the balance and pressure distribution with specific numerical values displayed on the display device, so that a verification burden to a surgeon is reduced and a precise, accurate, and fast operation is possible.

The battery 88 is a power supply for the pressure detection means 87, the rotation detection means 85, and the communication device, and is provided in a front portion of the detector 8 as shown in FIG. 14. The battery 88 may be removably mounted in the detector 8 or unitarily embedded in the detector 8. In the case in which the battery 88 is removably mounted, it is convenient in that the battery 88 can be separately charged. This advantage will be described later.

With reference to FIGS. 12 to 16, the balance checker 5 is a component to check balance between the distal end 913 of the femur 91 and the proximal end 931 of the tibia 93. The balance checker 5 includes an insertion portion 51 and an extension 53 extending from the insertion portion 51.

As the insertion portion 51, there are two types respectively called a first insertion portion 511 and a second insertion portion 513.

The first insertion portion 511 has a flat plate shape similar to the shape of the resected surface of the tibia 93 like the detector 8. The first insertion portion 511 is slightly larger than the detector 8. As the first insertion portion 511, there may be two first insertion portions that are provided at respective ends of the extension 53. With reference to FIG. 14, each first insertion portion 511 has an accommodation recess 5111 in an upper surface thereof.

With reference to FIG. 14, the accommodation recess 5111 is a recessed portion having a predetermined depth and a shape corresponding to the detector 8 to accommodate the detector 8. The first insertion portion 511 is further provided with an outer recess 5111a at one side of the accommodation recess 5111 such that the knob means 81 of the detector 8 can be received in the outer recess 5111*a* when the detector 8 is accommodated in the accommodation recess 5111 of the first insertion portion 511.

Figure 15:
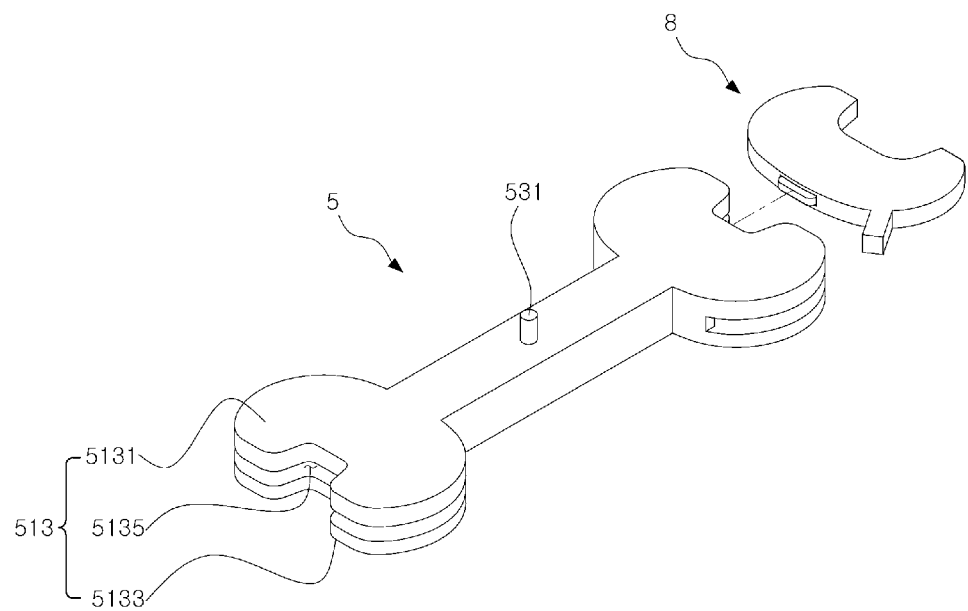
FIG. 15 is an exploded perspective view illustrating a balance checker and a detector according to another embodiment of the present invention.

With reference to FIG. 15, the second insertion portion 513 is composed of an upper plate 5131 and a lower plate 5133 having a shape similar to the shape of the resected surface of the tibia 93, and an insertion gap 5135 is provided between the upper plate 5131 and the lower plate 5133. The insertion gap 5135 is a space into which the detector 8 is inserted to detect the pressure and the rotation angle. The detector 8 slides into the insertion gap 5135 when it is mounted. In the case of installing the detector 8 in a sliding manner, it is not necessary to mount the detector 8 before installing the balance checker 5. That is, the balance checker 5 is first installed between the femoral component trial 71 and the tibia 93, and afterwards the detector 8 is inserted into the balance checker 5. In this case, since the detector 8 has the knob means 81, the detector 81 can be easily inserted and removed. For easy installation and removal of the detector 8, the insertion gap 5135 is deeply recessed in a position where the knob means 81 is located. Since the detector 8 needs to detect the pressure applied thereto in a state in which it is interposed between the upper plate 5131 an and the lower 5133, the upper plate 5131 and the lower plate 5133 are preferably made of a soft material that can be slightly deformed when pressed.

The extension 53 is connected between the two insertion portions 51 and provided with a checker laser device 531 at a middle portion thereof.

Figure 13:
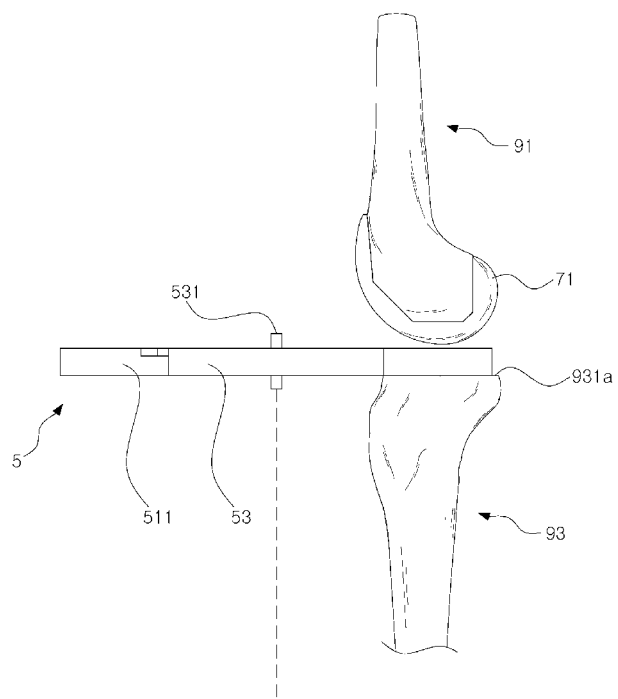
FIG. 13 is a side view illustrating a state in which the knee joint in which the balance checker is mounted is extended.

The checker laser device 531 is disposed in front of the tibia 93 when the insertion portion 51 is inserted between the femur 91 and the tibia 93, and emits a laser beam in a direction from the proximal end 931 to the distal end 933. The laser beam is used to check whether the balance checker 5 including the insertion portion 51 is well aligned with the bone. This alignment checking process is shown in FIG. 13. Next, the aligned knee joint undergoes medial and lateral balance checking while the knee joint is extended (see FIG. 16) and flexed (see FIG. 12).

With reference to FIGS. 17 to 20, the trial 7 includes a femoral component trial 71, a tibial component trial 73, and an insert trial 75.

The femoral component trial 71 is attached to the resected surface of the femur 91 and has the same shape as a femoral component serving as a cartilage. As described above, the femoral component trial 71 may include the reference rotation detection means 77.

The tibial component trial 73 is attached to the resected surface of the proximal end 931 of the tibia 93 and has the same shape as a tibial component serving as a cartilage. The tibial component trial 73 may include the positioning protrusion 7311 on an upper surface 731 thereof. The tibial component trial 73 may further include the reference rotation detection means 77.

The positioning protrusion 7311 is engaged with the positioning recess (refer to reference number 83 in FIG. 18) of the detector 8, thereby preventing the detector 8 from being separated from the trial 7 when the pressure and rotation of the trial 7 is checked with the detector 8.

The insert trail 75 is disposed between the femoral component trial 71 and the tibial component trial 73 and functions like a bearing. The insert trial 75 has an insert trial accommodation recess 751 in a lower surface thereof.

The insert trial accommodation recess 751 is a cavity to accommodate the detector 8. Therefore, the insert trial accommodation recess 751 has the same shape as the contour of the detector 8. An outer recess 751*a* is provided at one side of the insert trial accommodation recess 751 so that the knob means 81 of the detector 8 can be received in the outer recess 751*a*.

Next, a process of aligning a resection device for resecting a bone using the surgical instrument S described above during artificial knee joint replacement will be described.

With reference to FIGS. 5 to 9, the fixing portion 11 is attached to the distal end 913 of the femur 91. Next, the fixing portion fixing means 112 is inserted into the distal center fixation hole 1111 for temporary fixation.

Next, the connecting portion 17 is connected to the fixing portion 11 by inserting the connection hole insertion member 171 of the connecting portion 17 into the first connection hole 113 of the fixing portion 11. The ML laser device 1758 combined with the connecting portion 17 guides medial-lateral alignment on the coronal plane as illustrated in FIG. 7, and the AP laser device 1773 guides anterior-posterior alignment on the sagittal plane as illustrated in FIG. 8. At this time, the fixing portion rotation detection means 117 detects a rotation angle of the fixing portion 11 with respect to the femur 91 and displays the rotation angle on the external display device. A surgeon adjusts the rotation angle of the fixing portion 11 while checking the rotation angle displayed on the display device. Therefore, a precise and accurate operation is possible and a burden to a surgeon for verification of rotation of the fixing portion is reduced.

After the position adjustment of the fixing portion 11 is finished, another fixing portion fixing means 112 is inserted into the distal lopsided elongated hole 1113. Since the distal lopsided elongated hole 1113 is a long hole extending in a vertical direction, even when the fixing portion fixing means 112 are respectively inserted into the distal center fixation hole 1111 and the distal lopsided elongated hole 1113, the fixing portion 11 can be slightly rotated. When the position of the fixing portion 11 is finally determined after the rotation of the fixing portion 11 is finely adjusted, a further fixing portion fixing means 1114 is inserted into the distal lopsided fixation hole 1114, so that the fixing portion 11 is securely fixed not to be displaced. Since the fixing portion 11 is fixed by the three fixing portion fixing means, the fixing portion 11 can be securely fixed. The finished state of this process is shown in FIG. 9.

Next, with reference to FIG. 9, the connecting portion 17 is removed, and the first connection member 131 of the frontal cutting guide portion 13 is engaged with the first connection hole 113. Next, a cutting device such as a cutting saw is inserted into the frontal cutting guide slot 133 to resect a front portion of the femur. At this time, the fixing portion rotation detection means 117 detects whether the frontal cutting guide portion 13 combined with the fixing portion 11 is rotated by the force attributable of motion of the cutting device.

Next, the position of the distal cutting guide portion 15 is determined by inserting the second connection member 135 into the first connection recess 151 of the distal cutting guide portion 15. Next, fixing means such as pins are inserted into the frontal center fixation hole 1551 and the frontal inclined fixation hole 1553 such that the distal cutting guide portion 15 is fixed to the front side of the femur 91, and the frontal cutting guide portion 13 is removed. Finally, a cutting device such as a cutting saw is inserted into the distal cutting guide slot 153 and the distal end 913 of the femur 91 is resected by using the cutting device.

In the process described above, the frontal portion is resected first and then the distal portion is resected. However, this sequence is only exemplary and can be changed.

That is, the distal portion 913 may be resected first, and then the frontal portion may be resected.

With reference to FIGS. 10 to 11, the tibia cutting guide portion 31 is attached to the front side of the tibia 93 to resect the tibia 93. A fixing pin is first inserted into the tibia center fixation hole 3111 for temporary fixation of the tibia cutting guide portion 31, the connector 33 is attached to the tibia cutting guide portion 31, and medial-lateral alignment on the coronal plane can be performed using a laser beam emitted by the tibia laser device 3311. When the tibia cutting guide portion 31 is rotated while checking whether the axis of the tibia 93 is coincident with the laser beam, the guide portion rotation detection means 315 detects and sends a relative rotation angle of the tibia cutting guide portion with respect to the tibia 93 to the external display device. Therefore, a surgeon can rotate the tibia cutting guide portion 31 while checking the relative rotation angle from the external display device. Therefore, a precise and accurate surgical operation can be performed and a burden to a surgeon is reduced.

After the alignment of the tibia cutting guide portion is finished, a pin is inserted into the tibia inclined fixation hole 3113 to securely fix the tibia cutting guide portion 31 to the tibia. Preferably, three or more pins may be used. Next, a cutting device such as a cutting saw is inserted into the tibia cutting guide slot 313 to resect the proximal end 931 of the tibia 93. The operation rotation detection means 315 detects and sends a relative rotation angle of the tibia cutting guide portion to the external display device. Therefore, it is possible to check whether the tibia cutting guide portion 31 is displaced by the force attributable to motion of the cutting device.

With reference to FIGS. 12 to 16, the femoral component trial 71 is attached to the resected surface of the femur 91, and the insertion portion 51 of the balance checker 5 mounted with the detector 8 is inserted between the tibia 93 and the femoral component trial 71. In the case in which the second insertion portion 513 is provided in the balance checker 5, the detector 8 can be inserted into the balancer checker 5 in a sliding manner.

The checker laser device 531 emits a laser beam from the front side of the tibia 93 toward the distal end. Therefore, it is possible to check whether the balance checker 5 is aligned with the axis of the tibia using the laser beam.

Next, the knee joint is extended (see FIG. 16) and flexed (see FIG. 12) and the medial and lateral balance is verified. At this time, since the operation rotation detection means 85 included in the detector 8 detects a relative rotation angle of the balance checker 5 with respect to the femoral component trial 71, a precise adjustment can be performed while checking numerical values, and thus balance verification can be reliably performed.

In addition, the rotation and balance between the femur 91 and the tibia 93 can be easily verified using the pressure detection means 87. The term 'balance' may mean a difference in force distribution between a medial side and a lateral side of the knee joint, or a difference in force distribution between the case of extension and the case of flexion of the knee joint. When the difference in force distribution is large, the resection amount of the medial side, the lateral side, the distal side 913, or a rear side of the femur 91 is adjusted to obtain a desired balance state.

The pressure detection means 87 detects the distribution of pressure and displays it on an external display device. Therefore, a surgeon can easily and quickly perform an accurate surgical operation by checking the balance from the display device.

With reference to FIGS. 17 to 20, after the femoral component trial 71 is attached to the resected surface of the femur 91 and the tibial component trial 73 is attached to the resected surface of the tibia 93, the insert trial 75 equipped with the detector 8 that is accommodated in the accommodation recess 751 is inserted between the femoral component trial and the tibial component trial. Next, the balance is verified while extending and flexing the knee joint. At this point, the operation rotation detection means 85 included in the detector 8 detects a rotation angle of the insert trial 75 with respect to the femoral component trial 71. Therefore, it is possible to precisely adjust the rotation angle through numerical verification, thereby accurately and reliably verifying the balance.

In addition, it is possible to easily numerically verify the pressure distribution in accordance with rotation angles by using the pressure detection means 87. Herein, the balance may mean a difference in force distribution between a medial side and a lateral side of the knee joint, or a difference of force distribution between the case of extension and the case of flexion of the knee joint. When the difference in force distribution is large, the trial 7 is replaced with a larger size trial or an insertion angle of the trial is changed to obtain a suitable balance state.

As described above, since the pressure detection means 87 detects and sends a pressure distribution to the external display device, a surgeon can verify the balance using the information displayed on the external display device, so that the surgeon can easily perform a fast, precise, and accurate operation.

Figure 21:
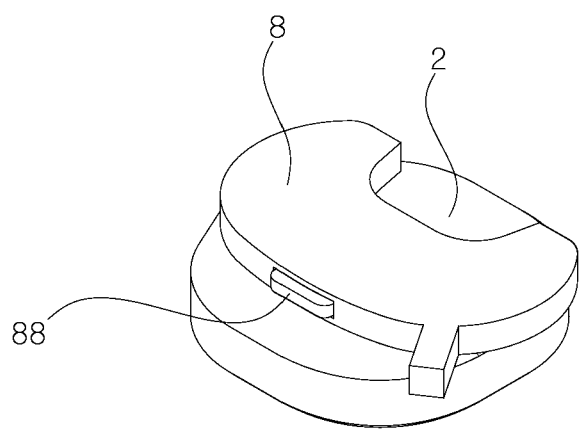
FIG. 21 is a perspective view illustrating a process of charging of the battery using a whole detector mounted with battery which is placed on charging means according to one embodiment of the present invention.
Figure 22:
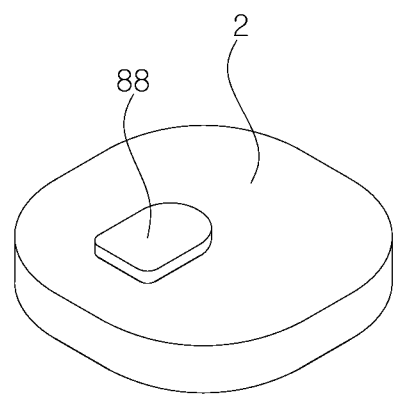
FIG. 22 is a perspective view illustrating a process of charging of battery using battery which is placed on charging means according to another embodiment of the present invention.

With reference to FIGS. 21 and 22, the battery 88 can be charged using an additional charging means 2. In this case, the charging means 2 transfers electric charges to the battery 88 in a wireless manner. Specifically, when the battery 88 is placed on the charging means 2, the battery is charged by radio frequency.

When the battery 88 is detachably mounted in the detector 8, as illustrated in FIG. 22, only the battery 88 can be placed on the charging means 2. However, when the battery 88 is embedded in the detector 8, as illustrated in FIG. 21, the whole detector 8 mounted with battery 88 is placed on the charging means 2 for charging of the battery 88.

The detailed description above is about an exemplary embodiment of the present invention. Although preferred embodiments of the present invention have been described for illustrative purposes, those skilled in the art will appreciate that various combinations, changes, and applications thereof are possible. The preferred embodiments can be changed or modified within the scope of the concept of the invention disclosed in the specification, the scope of equivalents, and/or the range of technologies or knowledge of those skilled in the art. The preferred embodiments that have been described above are best modes to realize the technical spirit of the present invention, and diverse changes required in application and use of the invention are also possible. In consequence, the detailed description is not intended to limit the scope of the invention but the scope of the following claims should be construed as including other embodiments.

What is claimed is:

1. A smart surgical instrument for artificial joint replacement, the surgical instrument comprising a femur resection device for resecting a femur, the femur resection device comprising:
   a fixing portion configured for attachment to a distal end of the femur; and
   a connecting portion connected to one side of the fixing portion, wherein the connecting portion comprises an medial-lateral laser device emitting a laser beam toward a proximal end of the femur from a front side of the femur and an anterior-posterior laser device emitting a laser beam toward the proximal end of the femur from a medial side or a lateral side of the femur when the fixing portion is attached to the distal end of the femur, thereby facilitating alignment of the fixing portion in a medial-lateral direction and an anterior-posterior direction.

2. The surgical instrument according to claim 1, wherein the femur resection device further comprises:
a cutting guide portion aligned with respect to the fixing portion.

3. The surgical instrument according to claim 2, wherein the cutting guide portion comprises a frontal cutting guide portion that guides cutting of a frontal portion of the distal end of the femur and a distal cutting guide portion that guides cutting of a middle portion of the distal end of the femur when the fixing portion is attached to the distal of the femur, and
the distal cutting guide portion is aligned by being connected to the fixing portion via the frontal cutting guide portion.

4. The surgical instrument according to claim 1, wherein the connecting portion comprises a medial-lateral member extending in the medial-lateral direction and an anterior-posterior member extending in the anterior-posterior direction, and
the medial-lateral member and the anterior-posterior member respectively comprise the medial-lateral laser device and the anterior-posterior laser device, thereby facilitating alignment of the fixing portion in the medial-lateral direction and the anterior-posterior direction.

5. The surgical instrument according to claim 1, wherein the fixing portion comprises a rotation detection means that enables numerical verification for a rotation state of the fixing portion during alignment of the fixing portion, which is performed by using a laser beam, thereby preventing the fixing portion from being displaced after the fixing portion is aligned.

6. The surgical instrument according to claim 5, wherein the rotation detection means is a gyro sensor.

7. The surgical instrument according to claim 1, further comprising a tibia resection device for resecting a tibia, wherein the tibia resection device comprises a laser device, whereby the surgical instrument enables eliminating a need of using an extramedullary aligner during alignment of the tibia for resection of the tibia.

8. The surgical instrument according to claim 7, wherein the tibia resection device comprises a tibia cutting guide portion attached to a frontal end of the tibia and a connector combined with the tibia cutting guide portion, and the connector comprises a laser device emitting a laser beam to a distal end of the tibia, whereby the surgical instrument facilitates alignment of the tibia cutting guide portion.

9. The surgical instrument according to claim 8, wherein the tibia cutting guide portion comprises a rotation detection means, thereby enabling numerical verification for an alignment state of the tibia cutting guide portion when the tibia cutting guide portion is aligned with a laser beam, whereby the surgical instrument enables alignment of the tibia cutting guide portion.

10. A surgical instrument for artificial joint replacement, the surgical instrument comprising:
a detector; and
wherein the detector comprises an operation rotation detection means detecting the rotation angle of a component of the surgical instrument and a pressure detection means, the pressure detection means being configured to be inserted between a tibial component trial and an insert trial, thereby allowing numeral verification for medial and lateral balance and for a rotation degree of the trials.

11. The surgical instrument according to claim 10, further comprising:
a reference rotation detection means providing a reference position used to detect a rotation angle of a component of the surgical instrument,
the operation rotation detection means detecting the rotation angle of the component with respect to the reference rotation detection means.

12. The surgical instrument according to claim 10, wherein the detector has a shape corresponding to a tibial component trial and a resected surface of the tibia.

13. The surgical instrument according to claim 10, wherein the tibial component trial has a positioning protrusion at one surface thereof to position the detector, and
the detector has the positioning recess at a position corresponding to the positioning protrusion so that the detector can be positioned on the tibial component trial and is prevented from slipping after being placed on the tibial component trial.

14. The surgical instrument according to claim 10, wherein the detector is equipped with a battery for supplying power to operate the operation rotation detection means and the pressure detection means, and the battery is charged through a wireless charging method.

15. The surgical instrument according to claim 14, wherein the battery is detachably mounted in the detector.

16. A surgical instrument for artificial joint replacement, the surgical instrument comprising a rotation detection means, a femoral component trial and a balance checker, the balance checker being configured for insertion between a tibia and a femur to check medial and lateral balance,
wherein the balance checker comprises a detector, and
the detector comprises an operation rotation detection means and a pressure detection means to allow numerical verification for medial and lateral balance and for a rotation state when the balance checker is inserted between the tibia and the femur.

17. The surgical instrument according to claim 16, wherein the balance checker comprises a first insertion portion provided with an accommodation recess in which the detector is accommodated, the detector is provided with a knob means at a periphery portion thereof, and the accommodation recess is provided with an outer recess at a position corresponding to the knob means such that the detector is removable from the balance checker.

18. The surgical instrument according to claim 16, wherein the balance checker comprises a second insertion portion composed of an upper plate and a lower plate such that the detector is inserted between the upper plate and the lower plate, whereby the detector is inserted into and removed from the balance checker in a sliding manner.

19. The surgical instrument according to claim 18, wherein the balance checker is equipped with a laser device at one side thereof, thereby allowing verification for an alignment state of the balance checker.

20. The surgical instrument according to claim 16, wherein the balance checker is equipped with a laser device at one side thereof, thereby allowing verification for an alignment state of the balance checker.

21. The surgical instrument according to claim 16, wherein the detector is equipped with a battery for supplying power to operate the operation rotation detection means and the pressure detection means, and the battery is charged through a wireless charging method.

22. The surgical instrument according to claim 16, wherein the detector has a shape corresponding to the resected surface of the tibia.

* * * * *